United States Patent [19]

Miller

[11] Patent Number: 4,624,251
[45] Date of Patent: Nov. 25, 1986

[54] APPARATUS FOR ADMINISTERING A NEBULIZED SUBSTANCE

[75] Inventor: Nicholas C. Miller, White Bear Lake, Minn.

[73] Assignee: Riker Laboratories, Inc., St. Paul, Minn.

[21] Appl. No.: 650,096

[22] Filed: Sep. 13, 1984

[51] Int. Cl.$^4$ .............................................. A61M 16/00
[52] U.S. Cl. ........................... 128/200.14; 128/205.24
[58] Field of Search ................. 128/200.11, 200.24, 128/200.19, 203.12, 203.14, 203.25, 204.13, 204.14, 205.11, 205.24, 200.14, 203.13, 204.26, 204.25, 204.21, 204.23, 205.18; 261/DIG. 65, 55

[56] References Cited

U.S. PATENT DOCUMENTS

| | | | |
|---|---|---|---|
| 1,169,996 | 2/1916 | Prindle | 128/205.24 |
| 2,914,064 | 11/1959 | Sandelowsky | 128/205.24 |
| 3,528,418 | 9/1970 | Grosholz et al. | 128/203.14 |
| 3,741,208 | 6/1973 | Jonsson et al. | 128/204.21 |
| 3,923,056 | 12/1975 | Bingmann et al. | 128/204.21 |
| 3,961,627 | 6/1976 | Ernst et al. | 128/204.21 |
| 4,106,503 | 8/1978 | Rosenthal et al. | 128/194 |
| 4,163,450 | 8/1979 | Kirk et al. | 128/204.23 |
| 4,508,117 | 4/1985 | Rodari | 128/205.24 |

Primary Examiner—Henry J. Recla
Attorney, Agent, or Firm—Donald M. Sell; James A. Smith; Robert W. Sprague

[57] ABSTRACT

An apparatus for administering a nebulized substance to a subject comprising a nebulizer and a valve assembly which permits continuous and constant flow of pressured gas through the nebulizer even when the apparatus is not being used to administer the substance to a subject. This steady state operation of the nebulizer provides for administration of a controlled dose of the substance. A method for administering a controlled dose to a subject is also described.

1 Claim, 3 Drawing Figures

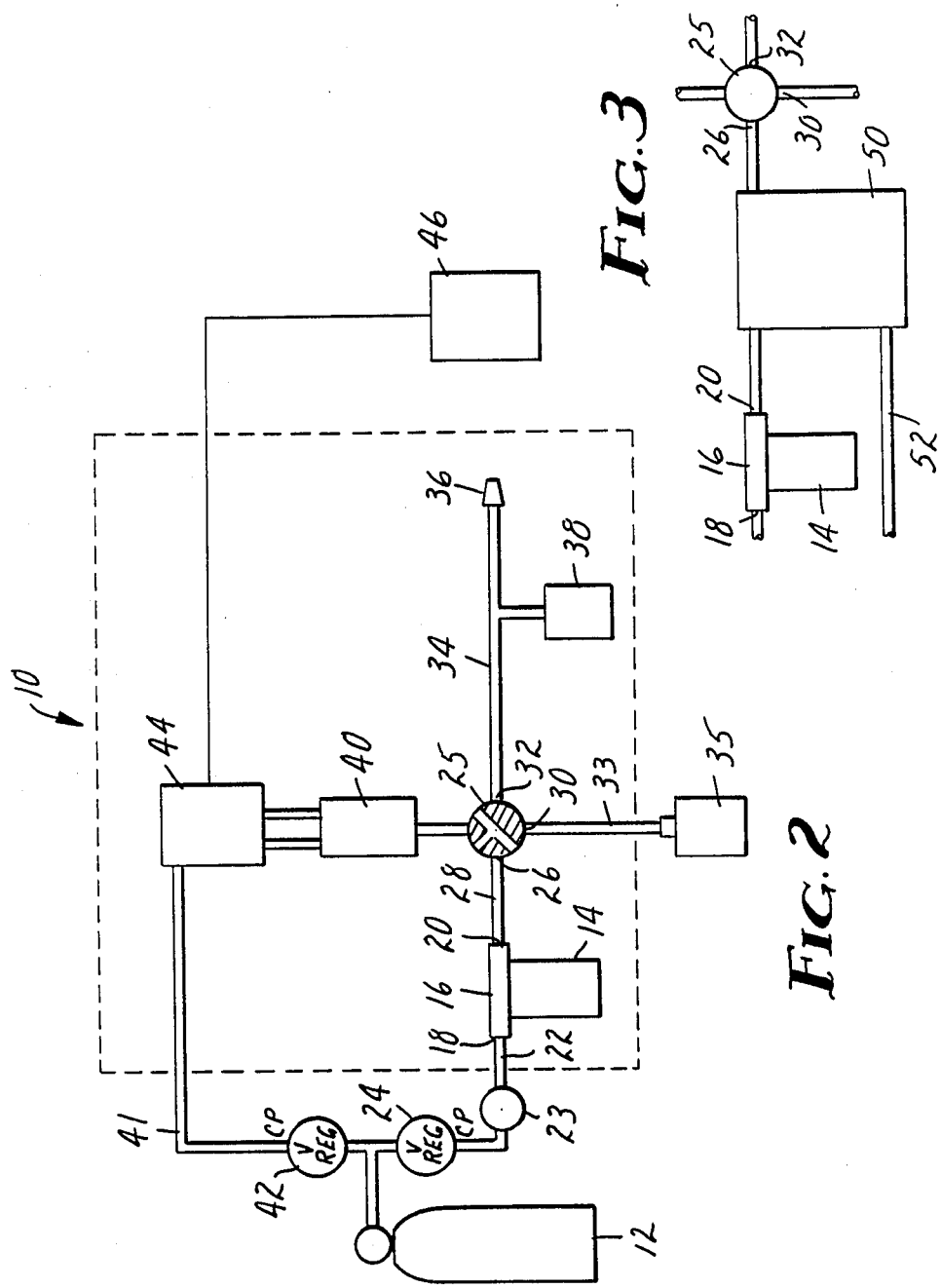

APPARATUS FOR ADMINISTERING A NEBULIZED SUBSTANCE

FIELD OF THE INVENTION

The present invention relates to a nebulizing apparatus and a method for administering a controlled amount of a substance to a subject.

BACKGROUND OF THE INVENTION

The present state of the art for delivering substances to the breathing passages of a subject in an aerosol form includes either formulation in and delivery from an aerosol container comprising a mixture of the substance to be delivered and a compressed gas, or a nebulizer, which utilizes a compressed gas from an outside source to carry the nebulized aerosol to the subject.

A system for delivering a metered dose of a nebulized antigen has been described and claimed by Rosenthal and French, U.S. Pat. No. 4,106,503. This system relies upon control of compressed air fed into a nebulizer to obtain a metered dose and includes a detector for sensing initiation of subject inhalation. It is not believed that a conventional nebulizer such as that described in U.S. Pat. No. 4,106,503 permits administration of a closely controlled dose of the substance since the nebulizer of such an apparatus is not given the opportunity to reach steady state operation prior to administration of a dose of the substance. That is, gas flows through the nebulizer only during actual administration of a dose. Upon initiation of gas flow, it is believed that substantial time is required before the size of the aerosolized droplets of the solution or suspension of the substance become essentially constant and to therefore permit administration of a closely controlled dose. The result is that the dose administered to the subject with such a device is not a well-controlled dose.

An apparatus which is capable of administering a closely controlled dose of an aerosol would be desirable such as for use in preliminary drug studies to determine, for example, whether a sufficient amount of an aerosol form of a new drug is absorbed through the lungs for that to be an efficacious route of administration. In studies such as these, the ability to administer a very closely controlled dose of the drug is important in order for measured blood levels of the drug and the like to be meaningful.

BRIEF SUMMARY OF THE INVENTION

The present invention provides a novel apparatus comprising a nebulizing means for generating an aerosol of a substance having a through opening comprising an inlet and an outlet, the inlet being coupled to a means for providing a supply of gas under pressure. Coupled to the outlet of the nebulizer means is an inlet of an administration means. The administration means includes an exhaust means, a delivery means, and a valve means for controlling the passage of aerosol through the delivery means. The exhaust means affords continuous and constant flow of gas through the nebulizing means when the apparatus is not being used to administer a dose to a subject. The delivery means is adapted to be coupled to the breathing passageway of a subject such as a patient. Finally, the apparatus includes an activating means for causing the valve means to permit passage of the aerosol through the delivery means for a predetermined period, after which the activating means returns the valve means to its normally closed position.

In the apparatus of the present invention, gas flow through the nebulizer need not be interrupted between administrations as is the case with prior art apparatus. As a result, the nebulizer means of the instant apparatus achieves steady state operation such that there is no significant variation in the concentration of substance in the gas flow or in the size of droplets of the aerosolized solution or suspension of the substance. This is in contrast to prior art devices such as that discussed above in which compressed gas flow is necessarily interrupted between administrations, and the nebulizer therefore requires substantial time after compressed air flow is reinitiated for it to reach steady state operation.

The present invention also provides a novel method for administering a controlled dose of a substance to a subject using the apparatus of the invention.

The apparatus and method of the present invention, since they permit administration of a closely controlled dose of an aerosolized substance, are particularly useful in drug studies to determine whether a medicament is efficacious when administered by inhalation in the form of an aerosol.

BRIEF DESCRIPTION OF THE DRAWING

The invention may be further illustrated by reference to the accompanying drawing wherein:

FIG. 2 is a block diagram of an alternative apparatus; and

FIG. 3 is a block diagram of a portion of still another alternative apparatus.

DETAILED DESCRIPTION OF THE PREFERRED EMBODIMENT

Figure 1:
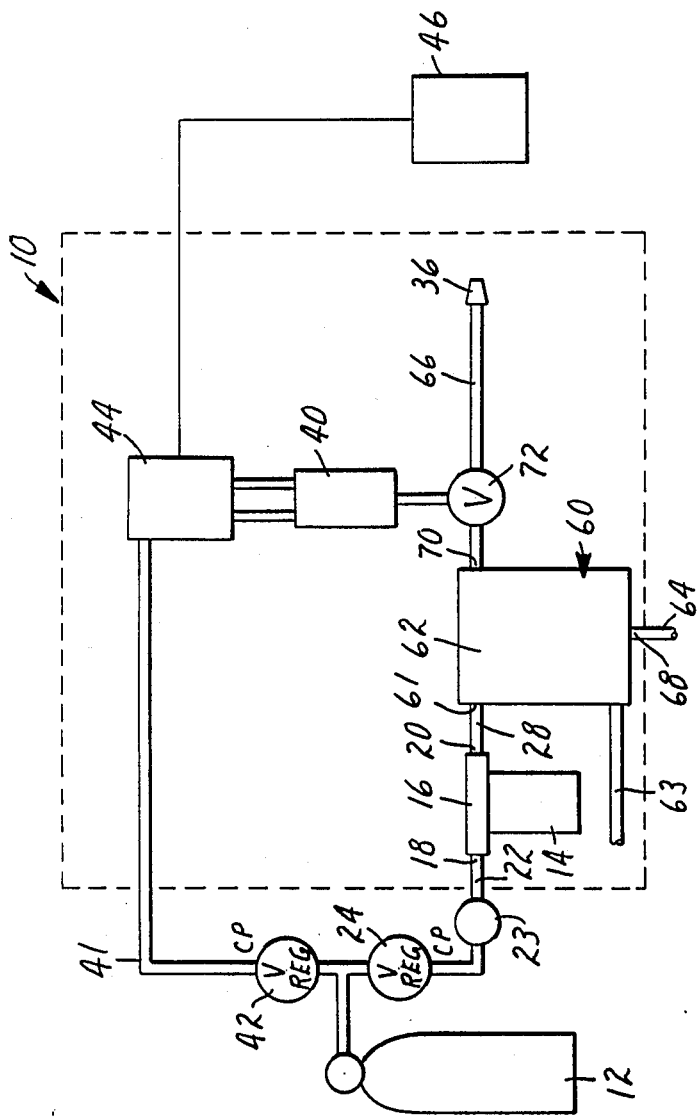
FIG. 1 is a block diagram of a preferred apparatus of the present invention.

As shown in FIG. 1 of the drawing, apparatus 10 comprises a compressed gas cylinder 12 as the means for providing a supply of gas under pressure. Typically, the gas employed will be air, but any inert, non-toxic gas may be used. Nebulizer 14 having through opening 16, inlet 18 and outlet 20 is coupled to cylinder 12 via high pressure flexible air hose 22 which includes, in its line, a two stage compressed air regulator 24 and flowmeter 23. Nebulizer 14 is a conventional nebulizer such as a Solo-sphere ® nebulizer, Model PH 2500 (commercially available from Airlife Corp., Montclair, CA), a Retec ® nebulizer (commercially available from Cavitron Corp., Long Island City, N.Y.), a Devilbiss Model 880 Ultrasonic Nebulizer (commercially available from the Devilbiss Company) or an Ohio Ball-Jet ® nebulizer (commercially available from Ohio Medical Products, Madison, Wisc.). Administration means 60 is coupled to outlet 20 of nebulizer 14 via inlet 61 using a tube 28 of inert plastic or metal. In the illustrated embodiment, administration means 60 includes mixing chamber 62, and an exhaust means 64 and a delivery means 66 which are coupled via a first outlet opening 68 and a second outlet opening 70, respectively.

Aerosol generated in nebulizer 14 passes through mixing chamber 62 where it is mixed with an externally sourced gas. The externally sourced gas is supplied through tube 63. The externally sourced gas will generally be controlled by a flowmeter (not illustrated). The externally sourced gas is generally the same as or compatible with the gas carrying the aerosol, and is used to dilute the aerosol and, independently of nebulizer 14, to adjust the concentration of the aerosolized substance. Employment of mixing chamber 62 is advantageous in situations where it is desirable to control particle size via the nebulizer and the concentration of the aerosol in an alternative way.

Exhaust means 64 and delivery means 66 comprise conventional tubing, and delivery means 66 further includes a mouth piece 36 suitable for permitting coupling of the apparatus with the breathing passages of the subject. A trap such as a water trap (not illustrated) may be coupled to the exhaust means 64 to prevent passage of the aerosolized substance into room air. It is the presence of exhaust means 64 which permits nebulizer 14 to operate steady state at all times, even between administrations of the aerosol to patients.

A cascade impactor or other dose sampling device by which the aerosolized dose may be scientifically examined may also periodically be connected to the exhaust means. Such devices are used to measure the size distribution, numerical distribution and dose, that is the quantity of the aerosolized substance.

In the illustrated embodiment, ball valve 72 is situated between second outlet opening 70 of administration means 60 and delivery means 66. Aerosol normally passes through the exhaust means only since ball valve 72 is normally closed to the passage of aerosol through delivery means 66. When it is desired to administer a dose of the aerosolized substance to a subject, it is an activating means which functions to cause ball valve 72 to open to permit aerosol to pass through the delivery means for a preset period of time. In the illustrated embodiment, the activating means comprises a pneumatic actuator 40 which is coupled to cylinder 12 via tubing 41 and a two-stage, adjustable pressure compressed air regulator 42 and solenoid pilot valve 44. The activating means further includes an adjustable, single shot delay timer 46 which is activated by a pushbutton (not illustrated). Timer 46, when activated, causes solenoid pilot valve 44 to supply compressed gas to pneumatic actuator 40 so as to cause ball valve 72 to open and to thereby permit aerosol to pass through delivery means 66. Thus, it is timer 46 which determines the period of time during which aerosol is permitted to pass through the delivery means. Typically, timer 46 is set for a period of usually ten seconds or less. Most commonly, timer 46 is set for a period of about 0.1 to 5 seconds.

FIG. 2 illustrates an alternative embodiment, again comprising cylinder 12 and nebulizer 14. Here, however, ball valve 25 is coupled to outlet 20 of nebulizer 14 via inlet 26 using a tube 28. Ball valve 25 includes first outlet opening 30 and second outlet opening 32, and functions to direct the aerosol generated in nebulizer 14 through only one of first outlet opening 30 and second outlet opening 32. As will be discussed in greater detail below, ball valve 25 normally directs all aerosol through first outlet opening 30. Coupled to first outlet opening 30 is an exhaust means which comprises conventional tubing 33 which may again be connected to, for example, a trap such as illustrated water trap 35 to prevent passage of the aerosolized substance into room air.

Coupled to second outlet opening 32 of ball valve 25 is a delivery means which comprises conventional tubing 34, a mouthpiece 36 suitable for permitting coupling of the apparatus with the breathing passages of the subject, and teflon check valve 38. Teflon check valve 38 is a one-way valve which allows air to enter the apparatus from the environment so as to be inhaled by the subject, but prevents aerosol and exhaled vapor from passing into the environment.

As indicated above, aerosol normally passes through the exhaust means. When it is desired to administer a dose of the aerosolized substance to a subject, it is an activating means which functions to cause ball valve 25 to direct all aerosol through second outlet opening 32 to the delivery means for a preset period of time, as opposed to directing the aerosol through first outlet opening 30 as it normally does. In this embodiment, the activating means again comprises pneumatic activator 40 which is coupled to cylinder 12 via tubing 41 and a two-stage, adjustable pressure compressed air regulator 42 and solenoid pilot valve 44. The activating means also again includes an adjustable, single shot delay timer 46 which is activated by a pushbutton (again not illustrated).

FIG. 3 shows yet another alternative apparatus wherein aerosol generated in nebulizer 14 passes through mixing chamber 50 where it is mixed with an externally sourced gas prior to passage to ball valve 25. The externally sourced gas is supplied through tube 52. Employment of mixing chamber 50 is advantageous for the reasons stated above in connection with the embodiment illustrated in FIG. 1.

While the activating means preferably includes a timer such as timer 46 shown in FIG. 1, the activating means may comprise alternative means for controlling the administration of a dose such as a flow meter which, by acting on the valve means, causes initiation of dose release at a certain air velocity associated with subject inhalation and terminates dose release after a predetermined volume of gas has passed through the meter.

The apparatus of the invention may be built to be used as is, or it may be built to be conveniently disassembled between uses. Disassembling and cleaning would allow the same apparatus to be used for delivering various substances.

The various substances which may be delivered via the apparatus of the invention include any substances which form aerosols when nebulized such as atropine and its salts, for example, atropine sulfate; various steroidal compounds such as beclomethasone and dexamethasone; sodium chloride; bronchodilators, for example, rimiterol, epinephrine, isoproterenol, albuterol, metaproterenol, isoetharine and the like; and various materials which are delivered via the pulmonary or nasal route, for example, substances not stable in the gastrointestinal tract, extensively metabolized by the liver or not readily absorbed by other routes. Some examples of the latter types of substances are peptides, hormones, insulin, heparin and the like. Other examples of materials which may be delivered via the apparatus of the invention are allergens, for example, when testing for allergic reactions. Further, the apparatus of the invention may be used for delivering contrast medium for X-rays.

The subject to which the dose of medicament is administered may be, for example, a human being or a laboratory test animal.

What is claimed is:

1. A device for delivering a metered dose of a substance, comprising:
   means for providing a supply of gas under pressure,
   nebulizing means for generating an aerosol of said substance, said nebulizing means defining a through opening having an inlet and an outlet, said inlet being coupled to said supply of gas, administration means for affording continuous and constant flow of gas through said nebulizing means and for affording administration of said aerosol to a subject, said administration means comprising a mixing chamber having first and second inlets and first and second outlets, said first inlet coupled to the outlet of said nebulizing means, a second means connected to said second inlet for providing a second supply of gas under pressure to said mixing chamber, an exhaust means coupled to the first outlet of said mixing chamber and open to the atmosphere which causes continuous and constant flow of gas through said nebulizing means, a delivery means coupled to said second outlet of said mixing chamber and; adapted to be coupled to the breathing passageway of a subject to permit administration of said aerosol to said subject, and valve means in said delivery means having parts relatively moveable between normally closed and open positions for controlling the passage of the aerosol through said delivery means, activating means for causing said valve means to permit passage of the aerosol through said delivery means for a predetermined period, after which said activating means returns said valve means to its normally closed position such that passage of aerosol through said delivery means is prevented.

* * * * *